United States Patent [19]
Camin et al.

[11] 4,272,503
[45] Jun. 9, 1981

[54] REDUCTANT COMPOSITION FOR TECHNETIUM-99M AND METHOD FOR MAKING TECHNETIUM-99M LABELLED LIGANDS

[75] Inventors: Leopoldo L. Camin, Lexington; Maria P. Liteplo, Bedford, both of Mass.

[73] Assignee: New England Nuclear Corporation, Boston, Mass.

[21] Appl. No.: 909,385

[22] Filed: May 25, 1978

[51] Int. Cl.³ .................... A61K 49/00; A61K 43/00
[52] U.S. Cl. ........................ 424/1; 23/230.3; 422/61; 424/1.5; 424/9
[58] Field of Search ...................... 424/1, 1.5, 9; 23/230.3; 422/61

[56] References Cited

U.S. PATENT DOCUMENTS 3,784,453   1/1974   Dworkin et al. ................... 424/1

OTHER PUBLICATIONS

Basmadjian et al., "Chemistry of Technitium Phosphate and Phosphonate Complexes: Application to Radio Pharmaceuticals" Private Communication.
Sewatkar, et al., Abstract of Meeting, 15 Internationale Jahrestagung der Gesellschaft für Nuclearmedizin, 13-16 Sep. 1977.
Basmadjian et al., "Abstract of Meeting 15 Internationale Jahrestagung. der Gesellschaft für Nuclearmedizin, 13-16 Sep. 1977.
Basmadjian et al., J. Nucl. Med., vol. 18, No. 6, 1977, p. 635.

Primary Examiner—Benjamin R. Padgett
Assistant Examiner—Christine M. Nucker
Attorney, Agent, or Firm—Sewall P. Bronstein; George W. Neuner

[57] ABSTRACT

Reductant compositions for reducing technetium to produce technetium labelled ligands comprise a substrate having attached thereto a reducing complex having sufficient redox potential to reduce technetium from the +7 oxidation state. Preferably the reducing complex comprises a reducing agent for technetium and a chelating ligand therefor. Technetium labelled ligands are prepared by mixing such ligands with pertechnetate in the presence of the reductant of this invention and separating the reductant from the resulting labelled ligand. Technetium labelled ligands that are substantially free from reducing agent used in their preparation may be made in this manner.

62 Claims, No Drawings

REDUCTANT COMPOSITION FOR TECHNETIUM-99M AND METHOD FOR MAKING TECHNETIUM-99M LABELLED LIGANDS

FIELD OF THE INVENTION

This invention relates to materials and methods for the preparation of technetium-99m labelled compounds, particularly technetium-99m radiopharmaceuticals, that require the reduction of technetium from the +7 oxidation state. More particularly, this invention relates to materials containing reducing agent for technetium immobilized on a separate or separable substrate, methods for using such materials to prepare technetium labelled compounds and the compounds prepared thereby.

BACKGROUND OF THE INVENTION

The use of tracer compounds, which emit radiation from within the body, as medical tools has long been known. Such materials have been used for testing liver function and biliary patency, for the analysis of the physiological structure and function of the kidneys, for imaging bone marrow, for scanning the skeletal bone structure of mammals, for blood pool imaging, for detecting tumors, and for analysis of the lungs, etc.

Another development in radionuclide use is the detection, location and assessment of infarcts in various areas of the body. An infarct is a region of dead tissue caused by complete interference with the blood supply to that tissue usually as the result of occlusion of the supplying artery. Infarcts can occur in essentially any area of the body, the most serious including infarcts in the brain and infarcts in myocardium or heart muscle, caused by thrombi, embolisms, arterial sclerosis, etc. A number of attempts have been made to use radionuclides to confirm the presence of infarcts, and to give an assessment of their size and situs.

Radioactively-labelled compounds which are selectively incorporated into infarcted tissue have been used for such purposes. Such agents include radioactive mercury derivatives of chlormerodrin and fluorescein, and technetium-labelled tetracycline, pyrophosphate and diphosphonates. See, Hubner, *Cardiovascular Research* 4:509 (1970) and Holman et al., *J. of Nuclear Medicine* 14:95 (1973).

Technetium-99m ($^{99m}$Tc) is a preferred radionuclide for radioactively scanning organs because of its short half-life and because it radiates gamma rays which can be easily measured, compared, for example, to beta rays. See *Radiology*, Vol. 99, April 1971, pages 192-196.

The use of technetium-99m in radiopharmaceutical form has become an important non-invasive method for diagnosis with wide ranging medical application because of its ready availability from a generator source, 140 KeV gamma radiation, and 6-hour half-life.

Technetium-99m is obtained from either extraction from Molybdenum-99 with a solvent such as methyl ethyl ketone or elution from a column of alumina or other support on which is adsorbed the parent isotope Molybdenum-99 with an aqueous media. The most stable chemical form assumed under these conditions is pertechnetate ($TcO_4^-$) in a +7 oxidation state. Most technetium-based radiopharmaceuticals, however, require a reduction to the +3, +4 or +5 oxidation state. Presently, these radiopharmaceuticals are frequently produced by combining an excess of the compound needed for labeling with a reducing agent, freeze-drying this mixture and adding pertechnetate.

Suitable reducing agents have been known for some time. Examples of such include divalent stannous ion ($Sn^{++}$) in the form of stannous chloride, tartrate, and phosphate, ferrous compounds ($Fe^{++}$), ferric-ascorbate complexes and reduced zirconium. Such reducing agents are used to bind radioactive $^{99m}$Tc to carriers, such as chelating agents, red blood cells, albumin and other proteins, and various other compounds which selectively seek out certain organs of the body, in order to carry the $^{99m}$Tc with them to such organs of the body where it is concentrated, whereby such organ can be radioactively scanned or imaged for diagnostic or other purposes, e.g. radioactive treatment of a pathological condition. See Journal of Nuclear Medicine, Vol. 11, No. 12, 1970, page 761; Journal of Nuclear Medicine, Vol. 12, No. 1, 1971, pages 22-24; Journal of Nuclear Medicine, Vol. 13, No. 2, 1972, pages 180-181; Journal of Nuclear Medicine, Vol. 12, No. 5, May 1971, pages 204-211; Radiology, Vol. 102, January 1972, pages 185-196; Journal of Nuclear Medicine, Vol. 13, No. 1, 1972, pages 58-65.

Generally a radiopharmaceutical product containing a technetium-99mm labelled ligand ($^{99m}$Tc-L) is made by mixing two components. A first component containing a reducing agent, such as stannous ions, and the ligand (L) to be labelled is mixed with radioactive pertechnetate solution from a generator to obtain the product. Thus, the radiopharmaceutical product contains technetium labelled ligand, stannous and stannic-ligand complexes, and excess ligand which is used to make sure that stannous or stannic salts do not precipitate out of solution and to reduce the quantity of free pertechnetate or reduced uncomplexed technetium in the solution, i.e. technetium that is not bound or complexed with the ligand.

Certain disadvantages can be found in the above procedure. First, although the reducing agent is not necessary for the functioning of the resulting radiopharmaceutical product, it remains in the product and is injected into the patient. While the presence of tin or other reducing agents generally used to make these products has not been found harmful, it is not desirable to inject unnecessary chemicals into a patient. Thus, it would be desirable to separate or eliminate the reducing agent from the final product.

Another disadvantage occurs when the ligand to be labelled is rare or difficult to obtain, or where the ligand to be labelled could be harmful to the patient and the amount injected must be minimized. Under such circumstances it is desirable to efficiently label small quantities of the ligand and not use any excess ligand in the labelling process.

U.S. Pat. Nos. 4,001,387; 3,902,849 and 3,749,556 describe radiopharmaceutical generator kits in which particulate or sintered reducing agent is used to reduce the technetium-99m. As described therein, the reducing agent absorbs the technetium-99m and then reduced technetium-99m is eluted using a solution of the ligand to be labelled. The eluate thus contains technetium-99m labelled ligand. The eluant may be passed through a strongly acidic ion exchange column to eliminate any uncombined reducing agent. Thus, apparently reducing agent-ligand complexes formed during reduction and elution remain in the product.

When stannous chloride is used conventionally as a reducing agent for labelling $^{99m}$Tc radiopharmaceuticals, the excess tin is also chelated by the compound being tagged. Excess uncomplexed tin often forms a colloid which interferes with the use of the product. For most $^{99m}$Tc labelled radiopharmaceuticals, tin is not an integral part of the Tc-complex but serves only as a reducing agent for pertechnetate. Therefore, it can be easily appreciated that a reduction/labeling system in which reducing agent is eliminated in the final labelled product would be highly desirable.

SUMMARY OF THE INVENTION

The present invention provides materials containing an immobilized reducing agent for technetium, methods for preparing radioactive ligands, particularly radiopharmaceuticals, using such materials, and radiopharmaceuticals produced thereby. Thus, one embodiment of this invention provides a reductant for reducing technetium comprising a substrate having attached thereto a reducing complex having sufficient redox potential to reduce technetium from the +7 oxidation state to an oxidation state at which the technetium forms a relatively stable complex with a ligand to be labelled. Preferably, the reducing complex comprises a reducing agent and a chelating ligand for binding the reducing agent to the substrate.

In another embodiment, this invention provides a method for providing technetium-99m labelled radiopharmaceuticals that comprises mixing a solution containing technetium-99m and a ligand to be labelled with a reductant for sufficient time to reduce substantially all of the technetium-99m and label said ligand to form technetium-99m labelled ligand, and separating said reductant from said technetium-99m labelled ligand, said reductant comprising a material in a separable phase comprising a substrate having attached thereto a reducing complex having sufficient redox potential to reduce technetium-99m from the +7 oxidation state to an oxidation state at which said technetium-99m forms a relatively stable complex with said ligand to be labelled. By "relatively stable complex" is meant a complex which does not dissociate within the period oftimes necessary for the use of the product. As is well known in the art, this period of time can vary from a few seconds up to a day or more depending on the particular diagnostic test being used.

In a preferred embodiment of this invention, technetium-99m labelled pharmaceuticals are provided that are substantially free from reducing agent.

DETAILED DESCRIPTION OF THE INVENTION

Technetium-99m labelled radiopharmaceuticals are generally prepared as needed by mixing a ligand (L) to be radioactively labelled and a reducing agent (R), such as, for instance, stannous chloride, with a solution of pertechnetate ($^{99m}$TcO$_4$−) in saline. The pertechnetate is reduced and technetium-99m labelled ligand ($^{99m}$TcL) is produced. This can be represented schematically as follows:

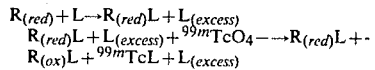

where $R_{(red)}$ is the reducing agent in its lower oxidation state and $R_{(ox)}$ is the reducing agent in its higher oxidation state. In such a process the reducing agent competes with technetium for sites on the ligand to be labelled and a large excess of ligand is required to insure that all of the reducing agent and all of the technetium are complexed so that they do not precipitate out of solution in use.

In accord with the present invention a reductant for reducing technetium and forming radiopharmaceuticals is provided that has the redox potential to reduce technetium but is not so readily available to compete with the technetium for sites to complex with the ligand to be labelled. Thus reductants of this invention are a separate or separable phase that can be easily separated from the technetium labelled pharmaceutical.

Generally, reductants in accord with this invention comprise a substrate having a reducing complex attached thereto. The reducing complex may be any well known material having sufficient redox potential to reduce technetium from the +7 oxidation state. Suitable reducing complexes include oxidation reduction polymers such as described by Cassidy, et al., *Oxidation-Reduction Polymers (Redox Polymers)*, Interscience Publishing (1965). Preferably, the reducing complex comprises a reducing agent for technetium and a chelating ligand for the reducing agent. Thus, a preferred reductant can be represented as

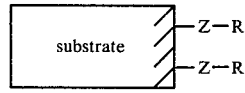

where Z is a chelating ligand for the reducing agent.

Any known reducing agent for technetium can be used to make the reductants of this invention. Preferably, the reducing agent is a metal ion that can be immobilized on a substrate by a chelating ligand. After complexing with the chelating ligand the reducing agent complex must have sufficient redox potential to reduce technetium-99m from the +7 oxidation state to produce $^{99m}$Tc ions capable of binding to the ligand being labelled. Suitable reducing agents include, for example, stannous ions, ferrous ions, cuprous ions, ferric-ascorbate complexes, and reduced zirconium. The stannous ion is a preferred reducing agent for technetium for many applications.

Chelating ligands for the above reducing agents are well known. See, for example, Cotton and Wilkinson, *Advanced Inorganic Chemistry*, Interscience Publishers (1962). Chelating ligands are compounds with one or more appropriate functional groups for binding with the reducing metal (in both its reduced and oxidized forms). Chelating ligands useful in this invention are those that can be bound to a substrate, either directly or through a linking group, and can bind the reducing agent. As is well known, preferred chelating ligands are compounds that contain multiple functional groups such as, for example, —SH, —COOH, —NH$_2$, and —OH phosphate and phosphonate groups. The number and configuration of such functional groups determine the ability of the compound to bind particular reducing agents. Preferably, the chelating ligand coordinates with the reducing agent forming a ligand-reducing agent complex that is more stable (either thermodynamically and kinetically) than a corresponding complex between the reducing agent and ligand to be labelled with technetium. Preferred chelating ligands include a polydentate ligand which forms a 1:1 ligand:reducing metal ion complex in such a way that the metal ion is coordinately saturated; a macrocyclic ligand of appropriate ring size, preferably one where all coordinating atoms are in a planar configuration; and a bicyclic or polycyclic ligand that can encapsulate the reducing agent.

Examples of chelating ligands for binding stannous ions include derivatives of ethylenediaminetetraacetic acid, 8-hydroxyquinoline, dihydrolipoamide, iminodiacetic acid, natural and synthetic macrocyclic complexes having multiple N, O, and/or S atoms, particularly those having 14–16 membered rings, such as cyclam, porphyrins, and corrins, etc., polycyclic ligands having N, O, and S atoms, e.g., cryptates such as [2,2,2] cryptate, sepulchrates, etc., and the like. Other suitable macrocyclic ligands are described in Lehn, "Cryptates: the chemistry of macropolycyclic inclusion complexes", *Acc. Chem. Res.*, 11, 49 (1978) and Christensen et al., *Chem Reviews*, 74, 351 (1974) which are hereby incorporated by reference.

Substrates useful in the practice of this invention include any material that is inert under conditions in which the reductant of this invention is used, that can be easily separated from the technetium labelled product and that can be bound substantially irreversibly to the chelating ligand or reducing complex either directly or through an intermediate group. By "substantially irreversibly" as used herein, we mean that the substrate and chelating ligand or reducing complex will maintain its bond under the conditions of use. Preferably, the bond is a covalent bond formed by reaction between the substrate and the chelating ligand or reducing complex.

Preferably, substrates useful herein are materials that can be made sterile and pyrogen-free. In addition, preferred substrates for the practice of this invention also have a large surface area which allows for attachment of a large number of metal chelating ligands. Suitable substrates include, for example, glass, and natural and synthetic polymers such as styrene-co-divinylbenzene and polysaccharides. Preferably such substrates are used in the form of particles or beads. In a particularly preferred embodiment, the substrate is the inside of a vial, for example, a glass vial that will contain the radiopharmaceutical, preferably etched for maximum surface area and derivatized to provide appropriate sites for attachment of metal chelating ligands that will be used to bind the reducing agent. It will be readily apparent to those skilled in the art that a vast number of substrates can be used to practice this invention. All such substrates are contemplated to be within the scope of this invention.

Substrates having chelating ligand already bound thereto are commercially available as functionalized glass beads, such as controlled porosity beads available from Corning Glass (such as CPG-550), and functionalized polysaccharide beads, such as those sold under the trademark Sepharose ® available from Pharmacia Fine Chemicals Co. Presently preferred substrate-chelating ligand materials include Corning CPG-ED3A and CPG-8-hydroxyquinoline,.

Reductants in accord with this invention are readily made. Some combinations of chelating ligand and substrate are available commercially and the reducing agent need only be chelated by mixing a solution of the reducing agent with the substrate-chelating ligand to bind the reducing agent thereto, and form the reductant of this invention. The reductant is then separated from the solution, rinsed to wash off any unbound reducing agent, and dried.

If a substrate having the desired chelating ligand is not available commercially, then the desired chelating ligand is attached to the substrate by known chemical reactions. For example, many chelating ligands can be attached to substrates having free hydroxy groups by the well known cyanogen bromide reaction. See, for example, Axen et al., "Chemical coupling of peptides and proteins to polysaccharides by means of cyanogen halides", nature, 214, 1302–1304 (1967). Other well known reactions will be readily apparent to those skilled in the art for particular combinations of substrates and chelating ligands. See, for example, Weetall, "Enzymes immobilized on inorganic carriers", *Res/Dev*, pp. 18–22 (Dec. '71); Bauman et al., "Coupled ligand chromatography applications to trace element collection and characterization", *Analyt Chem*, 39, 932–35 (1967); Gozdzicka-Jozefiak, "Preparation of chelating exchangers with a polysaccharide network and low cross-linkage", *J. of Chromatography*, 131, 91–97 (1977); Leyden et al, "Preconcentration of trace metals using chelating groups immobilized via silylation", *Analyt Chem*, 47, 9, pp. 1612–1616 (Aug. 1975); and Schmuckler, "Chelating resins-their analytical properties and applications", *Talanta*, 12, pp. 281–290 (1965).

Technetium-99m labelled ligands are prepared in accord with this invention by mixing the ligand to be labelled and pertechnetate ($^{99m}TcO_4^-$) in the presence of the above reductant. A schematic of the reaction is as follows:

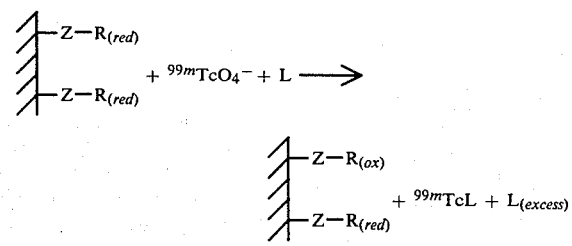

The reductant can then be separated from the technetium labelled product.

Any ligand capable of being labelled with technetium-99m can be labelled in accord with this invention. Particularly useful ligands are polyhydroxy polycarboxylic acids, aminocarboxylic acids, phosphonates, phosphates and mercaptans, etc. Examples of such ligands include, for instance, plasma proteins such as human serum albumin (HSA), ethylhydroxydiphosphonate (EHDP), methylenediphosphonate (MDP), pyrophosphate, ethylenediaminetetraacetic acid (EDTA), diethylenetriaminepentaacetic acid (DTPA), dimercaptosuccinic acid (DSMA), gluconate, glucoheptonate, N-(2,6-dimethylphenylcarbamoylmethyl)iminodiacetic acid (HIDA), analogs of HIDA such as N-(2,6-diisopropylphenylcarbamoylmethyl)iminodiacetic acid (PRIDA), N-(4-butylphenylcarbamoylmethyl)iminodiacetic acid (BIDA), clotting factors such as fibrinogen, gamma globulins, antibodies and their fractions, phytate, and the like.

When the reducing agent is bound to a substrate in accord with this invention, it does not readily compete with the reduced technetium-99m for sites on the ligand being labelled. Therefore less ligand is necessary to insure that free (not bound to a ligand) technetium-99m is at a minimum acceptable level in the product radiopharmaceutical. Thus this invention makes it more practical to label biologically active materials that are available in small quantities only and to label such materials having no native binding site and in which such a binding site is added synthetically.

As will be appreciated by those skilled in the art, the chelating ligand Z should be selected to provide a stable reductant under conditions of use. The chelating ligand should complex with the reducing agent to form a complex sufficiently stable (kinetically and/or thermodynamically) so that the reducing agent is not displaced by reduced technetium-99m and is not extracted by the ligand being labelled. Thus, it is readily apparent that the selection of the chelating ligand depends upon the particular ligand to be labelled and upon the particular using reducing agent being used. Preferably, the chelating ligand should have a stronger affinity for the reducing agent than for technetium-99m and the chelating ligand should have a stronger affinity for the reducing agent than the ligand to be labelled has for the reducing agent.

Chelating ligands that have been found useful, particularly when stannous ions are used for the reducing agent, include, for example, 8-hydroxyquinoline, dihydrolipoamide, iminodiacetic acid, derivatives of ethylenediaminetetraacetic acid, and the like.

Generally, radiopharmaceuticals can be prepared in accord with this invention so that there is less than 1.0 $\mu$g per ml of reducing agent (calculated on the basis of the reducing metal ion salt) in the product. Preferably, radiopharmaceuticals are prepared having less than 0.1 $\mu$g per ml of reducing agent on that basis, and most preferably less than 0.001 $\mu$g per ml. In accord with a particularly preferred embodiment of this invention, technetium-99m labelled pharmaceuticals are produced that are "substantially free" of reducing agent. By "substantially free" of reducing agent we mean that the reducing agent in the radiopharmaceutical product is less than 0.1 $\mu$g per ml on the above basis.

As will be readily appreciated by those skilled in the art, the quantity of reducing agent in the product can be minimized by proper selection of the chelating ligand for the particular reducing agent being used and ligand to be labelled, and by controlling the labelling conditions including the temperature and pH of the solution and the time that the solution is in contact with the reductant.

Therefore, to minimize the amount of reducing agent in the labelled product one should select a chelating ligand so that the reducing agent-chelating ligand complex is considerably more stable than the reducing agent-ligand to be labelled complex and so that a nonlabile reducing complex can be formed with the reducing agent. The reducing agent itself is preferably a nonlabile reducing metal ion (i.e. slow in making and breaking bonds). Optimal labelling conditions for minimizing the amount of reducing agent in the product include minimizing the quantity of ligand being labelled, minimizing the contact time between the reductant and the labelling solution, and minimizing the quantity of reductant.

It is also highly desirable to minimize the adsorption of technetium-99m by the reductant to obtain the technetium in the labelled product. This can be partially accomplished by following the criteria set forth above for minimizing reducing agent in the product. In addition, one should also select a chelating ligand so that the technetium labelled ligand complex is considerably more stable than a technetium-chelating ligand complex and should make sure that all possible binding sites on the chelating ligand are saturated with reducing agent.

Furthermore, it has been found that adsorption of technetium by the reductant can be minimized by increasing the quantity of ligand being labelled. Proper selection of the chelating ligand and reducing agent for the particular ligand being labelled will enable both reducing agent in the product and technetium adsorption by the reductant to be minimized.

It is readily apparent to those skilled in the art that various bond strengths and bond forming kinetics can be measured and/or calculated in order to select the appropriate chelating ligand and reducing agent for the particular ligand to be labelled. However, in practice it has been found simpler to conduct a series of tests using various combinations of chelating ligand and reducing agent for the reductant and to mix such reductant with the ligand to be labelled and pertechnetate for various lengths of time, from about 5 minutes to about 15 minutes being most suitable. At the end of such time the reductant and labelled ligand are separated and the labelled ligand is analyzed for the quantity of reducing agent and the reductant is analyzed for the quantity of adsorbed technetium.

The following examples are presented to further illustrate the practice of this invention.

EXAMPLE 1

A porous polyethylene frit of 0.25 cm thickness and average pore size of 70 $\mu$m was placed into a cylindrical glass column 7.0 cm high with an outer diameter of 1.0 cm and an inner diameter of 0.8 cm. Placed onto this was 0.5 mg. of Corning ED3A-CPG-550 controlled pore glass beads of 550 Å pore size with an ethylenediamine triacetic acid moiety convalently bonded onto the glass surface. Two rubber septa, 0.65 cm high and 0.85 cm in diameter, were pressed into the ends of the glass cylinder until their outer edges were flush with those of the cylinder. A hypodermic needle was inserted into the septum at the top of the column. A vacuum was induced in the column through this needle, and the process of evacuation was dynamically continued for several hours. After evacuation, the space within the column was filled to atmospheric pressure with nitrogen gas.

An admixture of 60 mg sodium glucoheptonate and 600 $\mu$g SnCl$_2$·2H$_2$O (spiked with Sn-113) in 1.50 ml deoxygenated water, pH 5.0, 0.2 molar sodium acetate-acetic acid buffer, was added to the nitrogen gas-filled column. This stannous loaded column was then placed on a vertical rotary mixer for 15 minutes.

After mixing, the stannous loading solution was removed via the bottom septum while a regulated 1 atmosphere of nitrogen gas simultaneously replaced the empty space.

A similar procedure was used with deoxygenated water to wash off any residual glucoheptonate or unbound stannous compounds.

An admixture of 1.0 mg of purified human serum albumin in 1.5 ml of 0.9% w/v aqueous sodium chloride adjusted to pH 2 with dilute HCl, and 12.3 mCi of technetium-99m as $^{99m}$TcO$_4^-$ was loaded onto the above column and vertically mixed for 15 minutes. The mixture was withdrawn from the column and placed in an evacuated vial. The column was then washed with 1.5 ml of 0.9% w/v aqueous sodium chloride. This wash was combined with the first sample and yielded a product containing 10.7 mCi of technetium-99m-labelled human serum albumin and 0.4 $\mu$g per ml of SnCl$_2$·2H$_2$O.

Samples of the above solution were injected into the tail vein of rats for evaluation as a radiodiagnostic blood pool imaging agent. Other samples were spotted on Gelman ITLC (SG) chromatography strips developed in methyl ethyl ketone (MEK) for determination of free pertechnetate.

Biodistribution results in rats 45 minutes after injection of 0.25 ml of the sample were as follows:

| % Injected Dose/Organ | |
| --- | --- |
| Blood* | 35.0 |
| Liver | 11.8 |
| Spleen | 1.1 |
| Lungs and Heart | 4.8 |
| Kidneys | 10.7 |
| Gastrointestinal Tract | 5.3 |
| Stomach | 0.4 |

*based on 5% body weight.

Free pertechnetate was 4.0% by ITLC (SG) in MEK.

EXAMPLE 2

A column was prepared and loaded with stannous as in Example 1, except that 20 mg of ED3A-CPG-550 beads were placed on the frit.

An admixture of 60 mg of glucoheptonic acid in 1.5 ml of 0.9% w/v aqueous sodium chloride adjusted to pH 8 with NaOH, and 94 mCi of technetium-99m as $^{99m}TcO_4^-$ was loaded onto the above column and vertically mixed for 15 minutes.

Samples of the above were withdrawn from the column and injected into the tail vein of rats for evaluation as a radiodiagnostic kidney imaging agent. Other samples were spotted on Gelman ITLC (SG) chromatography strips developed in 0.9% w/v aqueous sodium chloride and methyl ethyl ketone (MEK) for the determination of radiocolloid and free pertechnetate respectively.

Biodistribution results in rats 1 hour after injection of 0.25 ml of the sample were as follows:

| % Injected Dose/Organ | |
| --- | --- |
| Blood* | 1.5 |
| Liver | 0.7 |
| Kidneys | 21.8 |
| Intestines | 4.7 |
| Stomach | 0.1 |

*based on 5% body weight

Radiocolloid was 0.9% by ITLC (SG) in saline.
Free pertechnetate was 0.2% by ITLC (SG) in MEK.

EXAMPLE 3

A column was prepared and loaded with stannous as in Example 1, except that 20 mg of the ED3A-CPG-550 beads were placed on the frit.

An admixture of 1.0 mg tetrasodium pyrophosphate in 1.5 ml of 0.9% w/v aqueous sodium chloride, adjusted to pH 5 with dilute HCl, and 49.0 mCi of technetium-99m as $^{99m}TcO_4^-$ was loaded onto the above column and vertically mixed for 15 minutes.

Samples of the above solution were withdrawn from the column and injected into the tail vein of mice for evaluation as radiodiagnostic bone imaging agents. Other samples were spotted on Gelman ITLC (SG) chromatography strips developed in 0.9% w/v aqueous sodium chloride and methyl ethyl ketone (MEK) for determination of radiocolloid and free pertechnetate, respectively.

Biodistribution results in mice three hours after intravenous injection of 0.05 ml of the sample were as follows:

| % Injected Dose/Organ | |
| --- | --- |
| Blood* | 1.2 |
| Liver | 1.2 |
| Kidneys | 1.4 |
| Femur | 1.9 |
| Gastrointestinal Tract and Stomach | 3.6 |

*based on 5% body weight.

Radiocolloid was 3.4% by ITLC (SG) in saline.
Free pertechnetate was 6.2% by ITLC (SG) in MEK.

EXAMPLE 4

A column was prepared and loaded with stannous as in Example 1 except that (a) the immobilizing substrate-chelating ligand was BioRad chelating resin Chelex-100 ® which consists of a poly(styrene-co-divinylbenzene) with iminodiacetic acid convalently bonded thereto and (b) 20 mg (dry weight) of resin were placed on the frit.

An admixture of 1.0 mg of methylene diphosphonic acid in 0.9% w/v aqueous sodium chloride adjusted to pH 5 with NaOH and 71.2 mCi of technetium-99m as $^{99m}TcO_4^-$ in 1.5 ml total volume was added to the column and vertically mixed for 15 minutes.

Samples of the above solution were withdrawn from the column and injected into tail vein of mice for evaluation as radiodiagnostic bone agents. Other samples were spotted on Gelman ITLC8 SG) chromatography strips and developed in saline and methyl ethyl ketone (MEK) for determination of radiocolloid and free pertechnetate, respectively.

Biodistribution results in mice 1 hour after injection of 0.05 ml of the sample were as follows:

| % Injected Dose/Organ | |
| --- | --- |
| Blood* | 0.6 |
| Liver | 1.0 |
| Kidneys | 1.3 |
| Femur | 2.1 |
| Gastrointestinal Tract and Stomach | 2.1 |

*based on 5% body weight.

Free pertechnetate was 1.2% by ITLC (SG) in MEK.
Radiocolloid was 0.5% by ITLC (SG) in 0.9% w/v aqueous sodium chloride.

EXAMPLE 5

A column was prepared and loaded with stannous as in Example 1 except that (a) the immobilizing substrate-chelating ligand was BioRad chelating resin Chelex-100 ® and (b) 20 mg (dry weight) resin were placed on the frit.

An admixture of 20.0 mg of N-(2,6-dimethylphenyl-carbamoylmethyl)iminodiacetic acid (HIDA) in 1.5 ml of 0.9% w/v aqueous sodium chloride adjusted to pH 5 with NaOH and 20.6 mCi of technetium-99m as $^{99m}TcO_4^-$ was loaded onto the above column and mixed vertically for 15 minutes.

Samples of the above solution were withdrawn from the column and injected into the tail vein of mice for evaluation as radiodiagnostic hepatobiliary imaging agents. Other samples were spotted in Gelman ITLC (SG) chromatography strips and developed in 0.9% w/v aqueous sodium chloride for determination of radiocolloid.

Biodistribution results in mice 15 and 90 minutes after injection of 0.15 ml of the sample were as follows:

|  | % Injected Dose Organ | |
| --- | --- | --- |
|  | 15 minutes | 90 minutes |
| Blood* | 1.8 | 0.8 |
| Stomach | 0.4 | 0.4 |
| Intestines and Gall Bladder | 70.0 | 78.3 |
| Kidneys | 1.3 | 0.7 |
| Liver | 3.4 | 1.0 |

*based on 5% body weight.

Radiocolloid was 5.2% by ITLC (SG) in saline.

EXAMPLE 6

A porous polyethylene frit of 0.25 cm thickness and average pore size 70 μm was placed into a cylindrical glass column 7.0 cm high with an outer diameter of 1.0 cm and an inner diameter of 0.8 cm. Placed onto this was 100 mg of Corning-ED3A-CPG-550 controlled pore glass beads of 550 Å pore size with an ethylenediamine triacetic acid moiety covalently bonded onto the glass surface. Two rubber septa, 0.65 cm high and 0.85 cm in diameter were pressed into the ends of the glass cylinder until their outer edges were flush with those of the cylinder. A hypodermic needle was inserted into the septum at the top of the column. A vacuum was induced in the column through this needle. After evacuation, the space within the column was filled to atmospheric pressure with nitrogen gas.

An admixture of 200 mg sodium glucoheptonate and 100 μg $SnCl_2 \cdot 2H_2O$ (spiked with Sn-113) in 1.50 ml deoxygenated acetate buffer, 0.1 M, pH 5.0 was added to the nitrogen gas filled column. This stannous loaded column was then placed on a vertical rotary mixer for 20 minutes.

After mixing, the stannous loading solution was removed via the bottom septum, while a regulated 1 atmosphere of nitrogen gas simultaneously replaced the empty space.

A similar procedure was used with additional 1.5 ml aliquots of acetate buffer and 0.9% w/v aqueous sodium chloride adjusted to pH 3 to wash off any residual glucoheptonate or unbound stannous compounds.

An admixture of 25 mg of purified human serum albumin in 1.5 ml of 0.9% w/v aqueous sodium chloride adjusted to pH 2 with dilute HCl, and 2.7 mCi of technetium-99m as $^{99m}TcO_4-$ was loaded onto the above column and vertically mixed for 15 minutes. The mixture was withdrawn from the column and placed in an evacuated vial. The column was then washed with 1.5 ml of 0.9% w/v aqueous sodium chloride adjusted to pH 3. This wash was combined with the first sample and yielded a product containing 1.8 mCi of technetium 99m-labeled human serum albumin.

Samples of the above solution were injected into the tail vein of rats for evaluation as radiodiagnostic blood pool imaging agents. Other samples were spotted on Gelman ITLC (SG) chromatography strips developed in methyl ethyl ketone (MEK) for determination of free pertechnetate. An additional sample was fractionated on a column of Pharmacia Sephadex G100, eluted with 0.9% sodium chloride. The results were as follows:

% as $^{99m}TcO_4^{31}$ :5.5% by chromatography on ITLC/MEK;
% of Tc assoc. w̄ HSA:100% by gel filtration on G100;
Biodistribution in 2 rats, 45 min. after injection percent in blood:39±0%. (based on 5% of body weight)

EXAMPLE 7

ED3A-CPG-550 beads were loaded with stannous ions by the procedure used in Example 1. Variable quantities of the stannous loaded ED3A-CPG-550 were mixed with variable quantities of human serum albumin in the presence of Tc-99m-pertechnetate (∼10 mCi) in 1.5 ml of solution for 15 minutes to determine the amount of technetium adsorbed by the reductant. The results are given in the following table.

| Amount of $^{99m}Tc$ Adsorbed by Reductant | | |
| --- | --- | --- |
| Reductant Sn(II)-ED3A-CPG-550, mg | HSA, mg | %Tc on Reductant |
| 100 | 1 | 84 |
| 20 | 1 | 70 |
| 5 | 1 | 30 |
| 1 | 1 | 14 |
| 0.5 | 1 | 10 |
| 20 | 20 | 8 |
| 20 | 10 | .20 |
| 20 | 5 | 30 |
| 20 | 1 | 70 |

EXAMPLE 8

ED3A-CPG-550 beads were loaded with stannous ions by the procedure used in Example 1. Variable quantities of the stannous loaded ED3A-CPG-550 were mixed with variable quantities of N-(2,6-diisopropylphenylcarbamoylmethyl)-iminodiacetic acid (PRIDA) in the presence of Tc-99m-pertechnetate (∼10 mCi) in 1.5 ml of a solution for 15 minutes to determine the amount of Sn in the product based on the amount of Sn originally on the reductant. The results are given in the following table.

| Sn in Product When Labelling PRIDA | | | |
| --- | --- | --- | --- |
| Reductant Sn(II)-ED3A-CPG-550, mg | PRIDA mg | % Sn in Product | $SnCl_2 \cdot 2H_2O$ in product, μg/ml |
| 1 | 1 | 10 | 0.4 |
|  | 20 | 55 | 2.1 |
| 20 | 1 | 7 | 3.2 |
|  | 20 | 57 | 21 |

EXAMPLE 9

Tests were run the same as in Example 8 except using human serum albumin as the ligand being labelled. The results are given in the following table.

| Sn in Product When Labelling HSA | | | |
| --- | --- | --- | --- |
| Reductant Sn(II)-ED3A-CPG-550, mg | HSA, mg | % Sn in product | $SnCl_2 \cdot 2H_2O$ in Product μg/ml |
| 0.5 | 1.0 | 5 | 0.4 |
| 20.0 | 1.0 | 2 | 2.7 |

The above invention has been described in detail with particular reference to the preferred embodiments thereof, however, it will be appreciated that modifications within the spirit and scope of this invention may be effected by those skilled in the art.

We claim:

1. A product for reducing technetium comprising a substrate having attached thereto a reducing complex having sufficient redox potential to reduce technetium from the +7 oxidation state to an oxidation state at which said technetium forms a relatively stable complex with a ligand to be labelled.

2. The product of claim 1 wherein said reducing complex comprises a reducing agent and a ligand for binding said reducing agent to said substrate.

3. The product of claim 2 wherein said reducing agent is selected from the group consisting of stannous ions, ferrous ions, cuprous ions, ferric-ascorbate complexes, and reduced zirconium.

4. The product of claim 1 wherein said substrate is selected from glass and natural and synthetic polymers.

5. The product of claim 4 wherein substrate is in the form of particles.

6. The product of claim 4 wherein said substrate is the inside surface of a vial.

7. A product for reducing technetium comprising a substrate and a stannous reducing agent bound to the substrate by a chelating ligand.

8. The product of claim 7 wherein said chelating ligand is selected from the group consisting of natural and synthetic hetero macrocyclic ligands and hetero polycyclic ligands.

9. The product of claim 8 wherein said chelating ligand comprises a hetero macrocyclic ligand having a 14 to 16 membered ring.

10. The product of claim 7 wherein said chelating ligand is a multifunctional compound comprising functional groups selected from —SH, —COOH, —NH$_2$ and —OH.

11. The product of claim 7 wherein said chelating ligand is selected from 8-hydroxyquinoline, dihydrolipoamide, aminodiacetic acid and ethylenediaminetriacetic acid.

12. The product of claim 7 wherein said substrate is selected from glass and natural and synthetic polymers.

13. The product of claim 7 wherein said substrate is a material having free hydroxy groups.

14. A product for reducing technetium to form radiolabelled ligands comprising a stannous reducing agent bound to a substrate selected from glass and natural and synthetic polymers by a chelating ligand selected from 8-hydroxyquinoline, dihydrolipoamide, iminiodiacetic acid and ethylenediaminetriacetic acid.

15. The product of claim 14 wherein said substrate is the inside surface of a vial.

16. A method for preparing a technetium-99m labelled ligand comprising mixing the ligand to be labelled and pertechnetate in the presence of a reductant, said reductant comprising a substrate having attached thereto a reducing complex having sufficient redox potential to reduce technetium from the +7 oxidation state to an oxidation state at which said technetium forms a relatively stable complex with said ligand to be labelled, and separating said reductant from the technetium labelled ligand.

17. The method of claim 16 wherein said ligand to be labelled is selected from plasma proteins, gamma globulin, albumin, antibodies and fractions thereof, phytate, fibrinogen, a diphosphonate, a phosphate, a polyamino poly carboxylic acid, gluconate, glucoheptonate, and N-(2,6-dimethylphenylcarbamolymethyl) iminodiacetic acid and its analogs.

18. The method of claim 16 wherein said reducing complex comprises a reducing agent and a chelating ligand for binding said reducing agent to said substrate.

19. The method of claim 18 wherein said reducing agent is selected from the group consisting of stannous ions, ferrous ions, cuprous ions, ferric ascorbate complexes, and reduced zirconium.

20. The method of claim 16 wherein said substrate is selected from glass and natural and synthetic polymers.

21. The method of claim 20 wherein said substrate is particulate in form.

22. The method of claim 20 wherein said substrate is the inside of a vial.

23. A method for preparing a technetium-99m labelled ligand comprising mixing the ligand to be labelled and pertechnetate in the presence of a reductant, said reductant comprising stannous reducing agent bound to a substrate by a chelating ligand and separating said reductant from the technetium labelled ligand.

24. The method of claim 23 wherein said chelating ligand is selected from the group consisting of natural and synthetic hetero macrocyclic ligands and hetero polycyclic ligands.

25. The method of claim 24 wherein said chelating ligand comprises a hetero macrocyclic ligand having a 14 to 16 membered ring.

26. The method of claim 23 wherein said chelating ligand is a multifunctional compound comprising functional groups selected from —SH, —COOH, —NH$_2$ and —OH.

27. The method of claim 23 wherein said chelating ligand is selected from 8-hydroxyquinoline, dihydrolipoamide, iminodiacetic acid and ethylenediaminetriacetic acid.

28. The method of claim 23 wherein said substrate is selected from glass and natural and synthetic polymers.

29. The method of claim 23 wherein said substrate is a material having free hydroxy groups.

30. A method for preparing a technetium-99m labelled ligand comprising mixing the ligand to be labelled and pertechnetate in the presence of a reductant, said reductant comprising a stannous reducing agent bound to a substrate selected from glass and natural and synthetic polymers by a chelating ligand selected from 8-hydroxyquinoline, dihydrolipoamine, aminodiacetic acid and ethylenediaminetriacetic acid, and separating said reductant from the technetium labelled ligand.

31. The method of claim 30 wherein said substrate is the inside surface of a vial.

32. A radiopharmaceutical composition comprising technetium-99m labelled ligand and a reducing agent in an amount less than 1.0 μg per ml of composition.

33. The composition of claim 32 wherein said labelled ligand is selected from the group consisting of polyhydroxypolycarboxylic acids, aminocarboxylic acids, phosphonates, phosphates and mercaptans.

34. The composition of claim 33 wherein said labelled ligand is selected from plasma proteins, gamma globulin, albumin, antibodies and fractions thereof, phytate, fibrinogen, ethyhydroxydiphosphonate, methylenediphosphonate, pyrophosphate, ethylenediaminetetraacetic acid and derivatives thereof, diethylenetriaminepentaacetic acid, gluconate, glycoheptonate and N-(2,6-dimethylphenylcarbamoylmethyl) iminodiacetic acid and its analogs.

35. The composition of claim 32 wherein said composition is substantially free of reducing agent.

36. A container having therein a ligand to be labelled with technetium-99m for use as a radiopharmaceutical composition and a reductant comprising a substrate having attached thereto a reducing complex having sufficient redox potential to reduce technetium from the +7 oxidation state to an oxidation state at which said technetium forms a relatively stable complex with said ligand to be labelled.

37. The container of claim 36 wherein said ligand to be labelled is selected from plasma proteins, gamma globulin, antibodies and fractions thereof, phytate, fibrinogen, ethylhydroxydiphosphonate, methylenediphosphonate, ethylenediaminetetraacetic acid, diethylenetriaminepentaacetic acid, gluconate, glucoheptonate and N-(2,6-dimethylphenylcarbamoylmethyl) iminodiacetic acid and its analogs.

38. The container of claim 36 wherein said reducing complex comprises a reducing agent and a chelating ligand for binding said reducing agent to said substrate.

39. The container of claim 38 wherein said reducing agent is selected from the group consisting of stannous ions, ferrous ions, cuprous ions, ferric-ascorbate complexes, and reduced zirconium.

40. The container of claim 36 wherein said substrate is selected from glass and natural and synthetic polymers.

41. The container of claim 40 wherein said substrate is in the form of particles or beads.

42. The container of claim 40 wherein said substrate is the inside surface of said container.

43. A container having therein a ligand to be labelled with technetium-99m for use as a radiopharmaceutical composition and a reductant comprising a stannous reducing agent bound to a substrate by a chelating ligand.

44. The container of claim 43 wherein said chelating ligand is selected from the group consisting of natural and synthetic hetero macrocyclic ligands and hetero polycyclic ligands.

45. The container of claim 43 wherein said chelating ligand is a multifunctional compound comprising functional groups selected from —SH, —COOH, —NH$_2$ and —OH.

46. The container of claim 43 wherein said chelating ligand is selected from 8-hydroxyquinoline, dihydrolipoamide, aminodiacetic acid and ethylenediaminetriacetic acid.

47. The container of claim 43 wherein said substrate is selected from glass and natural and synthetic polymers.

48. The container of claim 43 wherein said substrate is a material having free hydroxy groups.

49. A container having therein a ligand to be labelled with technetium-99m for use as a radiopharmaceutical composition and a reductant comprising a stannous reducing agent bound to a substrate selected from glass and natural and synthetic polymers by a chelating ligand selected from 8-hydroxyquinoline, dihydrolipoamide, aminodiacetic acid and ethylenediaminetriacetic acid.

50. The container of claim 49 wherein said substrate is the inside surface of said container 51. A product for reducing technetium comprising a substrate having attached thereto a reducing complex having sufficient redox potential to reduce technetium from the +7 oxidation state to an oxidation state at which said technetium forms a relatively stable complex with a ligand to be labelled, said substrate being sterile and inert under the conditions under which said product is used.

52. The product of claim 51 wherein said reducing complex comprises a reducing agent and a ligand for binding said reducing agent to said substrate.

53. The product of claim 52 wherein said reducing agent is selected from the group consisting of stannous ions, ferrous ions, cuprous ions, ferric-ascorbate complexes, and reduced zirconium.

54. The product of claim 51 wherein said substrate is glass.

55. The product of claim 54 wherein said substrate is in the form of particles.

56. The product of claim 54 wherein said substrate is the inside surface of a vial.

57. The product of claim 51 wherein said substrate is a natural or synthetic polymer.

58. The product of claim 51 wherein said reducing complex comprises a stannous reducing agent bound to the substrate by a chelating ligand.

59. The product of claim 58 wherein said chelating ligand is selected from the group consisting of natural and synthetic hetero-macrocyclic ligands and hetero-polycyclic ligands.

60. The product of claim 59 wherein said chelating ligand comprises a hetero-macrocyclic ligand having a 14 to 16 membered ring.

61. The product of claim 58 wherein said chelating ligand is a multifunctional compound comprising functional groups selected from —SH, —COOH, —NH$_2$ and —OH.

62. The product of claim 58 wherein said chelating ligand is selected from 8-hydroxyquinoline, dihydrolipoamide, aminodiacetic acid and ethylenediaminetriacetic acid.

* * * * *

UNITED STATES PATENT AND TRADEMARK OFFICE
CERTIFICATE OF CORRECTION

PATENT NO. : 4,272,503
DATED : June 9, 1981
INVENTOR(S) : Leopoldo L. Camin and Maria P. Liteplo It is certified that error appears in the above-identified patent and that said Letters Patent are hereby corrected as shown below:

Col. 2, line 25, change "99mm" to ---99m---.

Col. 2, line 59, change "then" to ---the---.

Col. 2, line 62, change "eluant" to ---eluate---.

Col. 10, line 35, change "ITLC8SG)" to ---ITLC(SG)---.

Col. 12, line 1, change "% as $^{99m}TcO_4^{31}$: 5.5%" to

---% as $^{99m}TcO_4^{-}$: 5.5%---.

Signed and Sealed this

Sixteenth Day of February 1982

[SEAL]

Attest:

Attesting Officer

GERALD J. MOSSINGHOFF

*Commissioner of Patents and Trademarks*